(12) United States Patent
Hince

(10) Patent No.: US 6,620,611 B2
(45) Date of Patent: Sep. 16, 2003

(54) SOLID-CHEMICAL COMPOSITION FOR SUSTAINED RELEASE OF ORGANIC SUBSTRATES AND COMPLEX INORGANIC PHOSPHATES FOR BIOREMEDIATION

(75) Inventor: Eric Christian Hince, Campbell Hall, NY (US)

(73) Assignee: Geovation Technologies, Inc., Florida, NY (US)

( * ) Notice: Subject to any disclaimer, the term of this patent is extended or adjusted under 35 U.S.C. 154(b) by 0 days.

(21) Appl. No.: 09/755,473

(22) Filed: Jan. 6, 2001

(65) Prior Publication Data

US 2002/0090697 A1 Jul. 11, 2002

(51) Int. Cl.⁷ .............. B09B 3/00; C02F 3/00; C12N 9/98; C12N 11/10; C12N 11/12
(52) U.S. Cl. ............ 435/262.5; 210/600; 210/610; 435/176; 435/178; 435/179; 435/187; 435/243; 435/252.5; 435/252.7; 435/253.3; 435/254.22; 435/254.3
(58) Field of Search .................. 424/406, 407, 424/489, 493, 494, 496, 500, 78.08, 93.1, 93.4, 93.7, 94.1, 725, 780; 435/262.5; 210/600, 610

(56) References Cited

U.S. PATENT DOCUMENTS

| | | | |
|---|---|---|---|
| 5,062,956 A | | 11/1991 | Lupton et al. |
| 5,476,992 A | * | 12/1995 | Ho et al. |
| 5,554,290 A | | 9/1996 | Suthersan |
| 5,580,770 A | * | 12/1996 | DeFilippi |
| 5,582,627 A | * | 12/1996 | Yamashita |
| 5,681,739 A | | 10/1997 | Turick et al. |
| 5,753,254 A | * | 5/1998 | Khan et al. |
| 5,840,338 A | * | 11/1998 | Roos et al. |
| 5,968,359 A | | 10/1999 | Krahn et al. |
| 6,066,772 A | | 5/2000 | Hater et al. |
| 6,083,293 A | * | 7/2000 | Bath |

OTHER PUBLICATIONS

E.K. Nyer and S. Suthersan, InSitu Reactive Zones, GWMR, Summer 1996, pp 70–75.
E. Nyer, F. Lenzo, and J. Burdick, InSitu Reactive Zones: Dehalogenation of Chlorinated Hydrocarbons, GWMR, Spring 1998, pp. 68–72.

* cited by examiner

*Primary Examiner*—David M. Naff
*Assistant Examiner*—Deborah K. Ware

(57) ABSTRACT

A slow-release solid chemical composition for environmental bioremediation is provided. The composition comprises a source of soluble organic substrates which include sugars, soluble organic polymers and mixtures of them in an amount of 7% to 90%, insoluble organic substrates an amount of 10% to 70%, complex inorganic phosphates in an amount of 0.5% to 7% and soluble organic salts in an amount of 2% to 70%. The insoluble organic substrates include fibrous plant materials, starches, cellulosic materials and mixtures of these substrates. The complex inorganic phosphates include ringed metaphosphates, linear polyphosphates and mixtures. The organic salts include lactates, formates, acetates, citrates, etc. Also the composition further comprises microorganisms which include Bacillus spp., Rhizobium spp., Bradyrhibzobium spp., Fibrobacter spp., Clostridium spp., Pseudomonas. spp., Geobacter spp., Arthrobacter spp., Nocardia, spp., aspergillus spp., Trichoderma spp., Candida spp., Yarrowia spp. and combinations of these microorganisms. The composition can be prepared in various forms, including granules, briquettes, pellets, tablets or capsules.

29 Claims, 2 Drawing Sheets

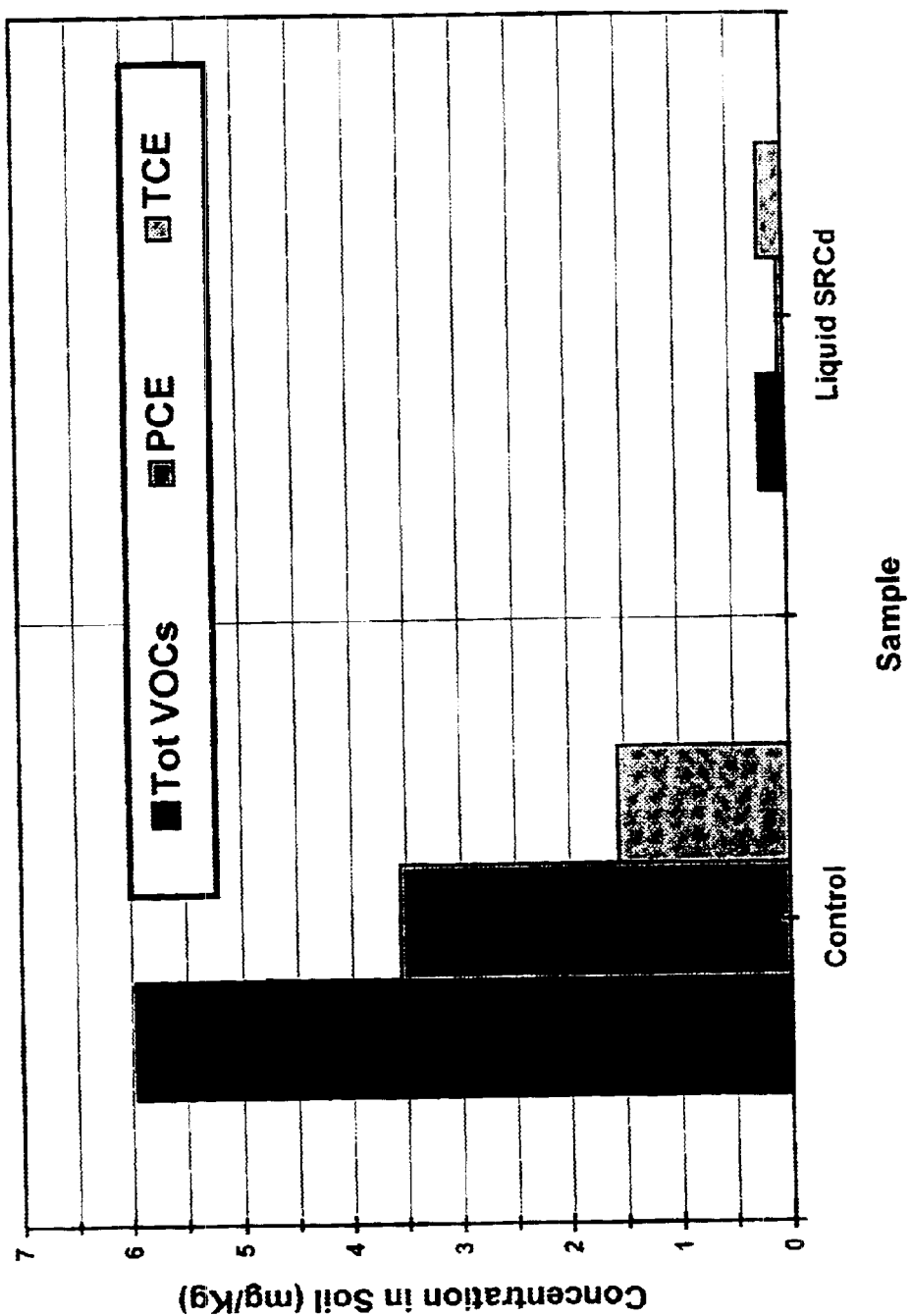

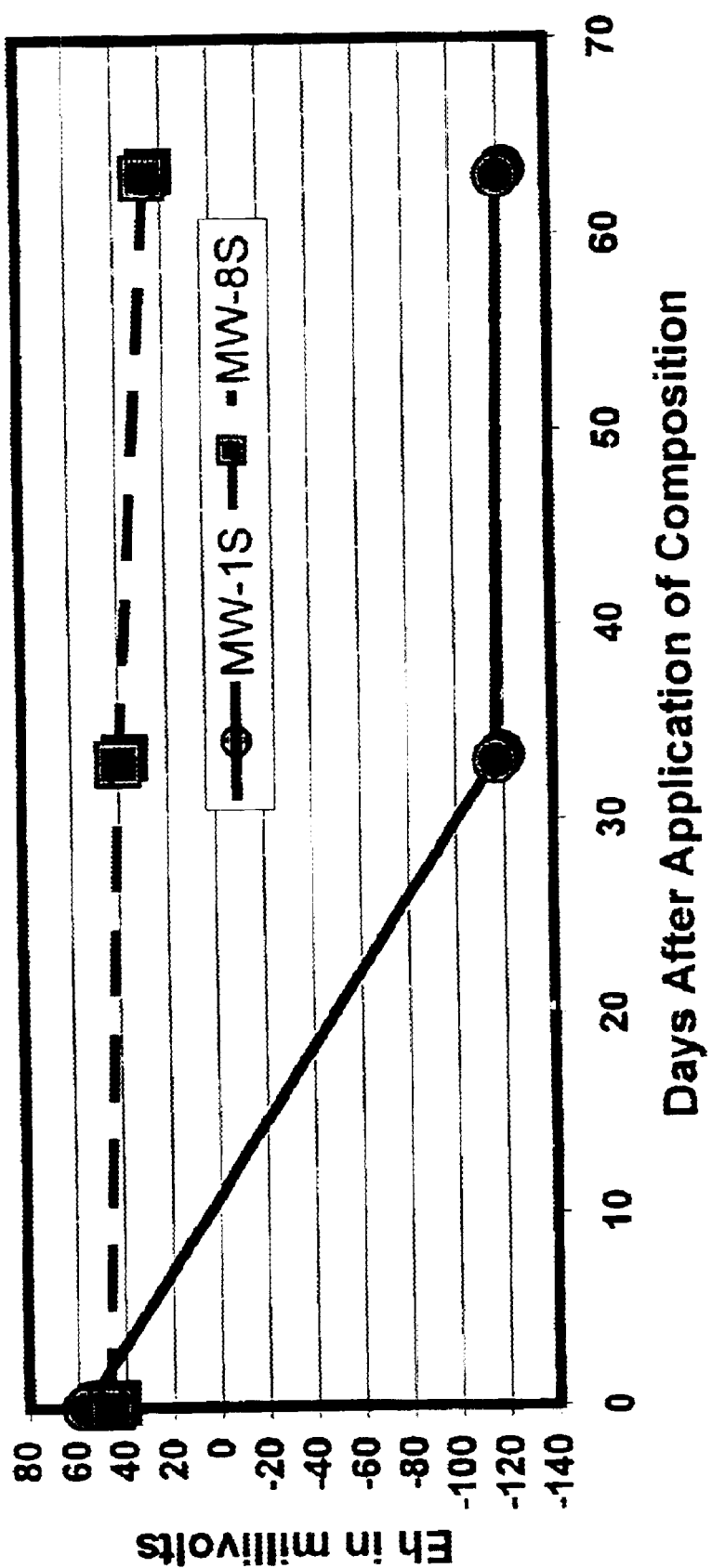

SOLID-CHEMICAL COMPOSITION FOR SUSTAINED RELEASE OF ORGANIC SUBSTRATES AND COMPLEX INORGANIC PHOSPHATES FOR BIOREMEDIATION

BACKGROUND—FIELD OF THE INVENTION

This invention discloses advanced solid-chemical compositions which provide balanced, sustained-release sources of soluble and insoluble organic substrates and complex inorganic phosphates, as well as other beneficial agents, which when used as intended, promote the bioremediation of contaminated environmental media. Specifically, the present invention was developed to provide a relatively simple and inexpensive means of enhancing the anaerobic bioremediation and dehalogenation of halogenated organic contaminants, such as trichloroethene (TCE), as well as the biologically mediated chemical reduction of oxidized forms of certain inorganic contaminants, such as chromium (VI), uranium (VI), and arsenate-based pesticides. Either alone or in combination with other liquid- and solid-chemical compositions, it is the inventor's belief that the present invention also has the potential for the remediation of the gasoline additive methyl tertiary butyl ether (MTBE).

The disclosed solid-chemical compositions of the present invention provide improved means for (1) creating, enhancing, and maintaining anaerobic if not anoxic conditions by facilitating the biologically mediated removal of the available oxygen from the media; and (2) creating and maintaining reducing conditions (i.e., negative Eh values) and near neutral to slightly acidic pH conditions ($6 \leq pH \leq 8$) which favor anaerobic, biologically mediated chemical-reduction reactions, e.g., the reductive dehalogenation of halogenated organic contaminants and the reduction of the oxidized forms of certain metals. The disclosed solid-chemical compositions also provide means for maintaining the aforementioned conditions for sufficiently long periods of time to enable the biologically mediated degradation, transformation, and/or detoxification reactions to proceed to the extent that the concentrations and/or toxicity of the contaminants are reduced to acceptable levels.

BACKGROUND—DESCRIPTION OF PRIOR ART

Soil and ground-water pollution caused by chemical contaminants released into the environment is a well documented, world-wide problem. Such chemical contamination is associated with many different types of industrial activities over the last two centuries. Common environmental contaminants include several different types and forms of petroleum hydrocarbons, halogenated organic compounds including solvents (e.g., tetra- and trichloroethene, methylene chloride), organochlorine pesticides (e.g., DDT and toxaphene), polychlorinated biphenyls (i.e., PCBs), and heavy metals and other inorganic contaminants such as cyanides. The available toxicological data indicates that many of these contaminants, in particular many of the halogenated organic compounds, are toxic, carcinogenic or potentially carcinogenic to humans, animals and other environmental receptors. In addition, the available environmental and ecological data have shown that many of these contaminants tend to persist in the environment for long time periods. The long-term stability and extremely slow degradation of many such environmental contaminants presents a substantial, long-term hazard to human health and the environment throughout the industrialized world.

Many of the so-called conventional methods for the remediation or clean-up of chemically contaminated wastes, waters, soils, and sediments have generally involved either the physical removal of the contaminated media or the simple mass transfer of the contaminants from one media (e.g., soil) to another (e.g., air). In general, such physical-treatment technologies do not involve the chemical and/or biological destruction, breakdown, transformation, or detoxification of the contaminants. Two of the most common categories of physical environmental-remediation technologies are the excavation and off-site disposal (or treatment) of contaminated soils and the pumping and subsequent treatment of contaminated ground water. The excavation of contaminated soils is often followed by their disposal in a landfill, which can pose a potential long-term risk to the environment, or their incineration, which may result in the release of air pollution. Many ground-water pump-and-treat processes involve the simple mass-transfer or "stripping" of the contaminants from the water into the air. Another common physical-treatment method involves the use of granular activated carbon (GAC) reactors to treat chemically contaminated waters. When contaminated water is passed through a GAC reactor, the contaminants are physically adsorbed onto the carbon particles, thereby producing another contaminated media which requires subsequent disposal and/or treatment. Each of these physical-treatment technologies share the same disadvantage—they do not reduce the actual amount or toxicity of the chemical contaminants, but rather they simply move the contamination from one place to another or from one media to another.

Another category of environmental-remediation technologies, termed bioremediation, involves the use of microorganisms to convert chemical compounds into innocuous or less harmful chemical compounds. Bioremediation technologies generally have lower costs associated with their use and implementation than do the competing physical technologies. Bioremediation technologies can also be adapted to a broader range of contamination problems and variations in field conditions than other types of remediation technologies.

The most promising bioremediation technologies provide the additional capability of treating contaminated media in-situ, i.e., in place, without the need for ground-water pumping or soil excavation. Current trends in bioremediation technology indicate that the most technically feasible and commercially successful bioremediation technologies are those which promote bioremediation processes mediated by indigenous or "native" contaminant-degrading bacteria, fungi and other microorganisms which are naturally present in the, contaminated media. The presence of naturally occurring, contaminant-degrading microorganisms in many different types of environmental media has been extensively documented in the scientific literature. There is an extensive body of prior-art literature and patents concerning various means of using both aerobic and anaerobic bioremediation processes, engineered bacteria, and the "bioaugmentation" of contaminated media with cultured microorganisms and fungi to promote the biodegradation of organic contaminants in water, soil, and industrial wastes. For example, it has been reported that native Alcaligenes spp., Pseudomonas spp., and Enterobacter spp. can degrade a number of pesticides and polychlorinated biphenyls (Nadeau et al., 1994, *Applied and Environmental Microbiology;* Aislabie et al., 1997, New Zealand *Journal of Agricultural Research;* Galli et al., 1992, *Pseudomonas: Molecular Biology and Biotechnology*). Recent trends in the art and literature acknowledge a growing understanding of the use of anaerobic biological processes in the treatment of many different types of contaminants that are otherwise recalcitrant under aerobic conditions. In particular, trends in the art reflect a growing understanding of the need and importance of achieving and maintaining anaerobic conditions and other factors which favor the biologically mediated chemical reduction, dehalogenation, biodegradation, transformation, and/or detoxification of recalcitrant organic and inorganic contaminants in the environment.

U.S. Pat. No. 6,066,772 to Hater et al. (to Waste Management, Inc. and International Technologies Corporation) discloses a two-step, biologically mediated process for converting hazardous explosives such as nitroaromatic and nitramine explosives in soil, resulting in soils free of explosive contaminants and their reduced derivatives. The anaerobic step involves mixing natural microorganisms and an oxidizable carbon source (e.g., dextrose, molasses, beet juice, potatoes, sweet potatoes, corn starch, potato starch) into the soil to produce reduced residues of the explosives. The second, aerobic step involves mixing the resultant reduced residues with a compostable material (e.g., grass clippings, yard waste, municipal solid waste, landfill compostable materials) and aerating via mechanical agitation or introduction of pressurized air. Hater et al. do not disclose the application of their process for the treatment of environmental media other than soil, nor do they disclose the application of their process to the remediation of contaminants other than explosives. Hater et al. do not disclose the formulation or use of solid-chemical compositions, such as those disclosed in the present invention, which provide for a sustained-release of soluble and insoluble substrates and complex inorganic phosphates. Hater et al. also do not disclose the application or use of additional nutrients or beneficial agents disclosed herein. Hence, Hater et al. do not disclose the present invention.

U.S. Pat. No. 5,062,956 to Lupton et al. discusses a method of reducing soluble Cr(VI) using fermentative, sulfate-reducing anaerobic bacteria to reduce Cr(VI) to Cr(III) and immobilize the latter as the extremely insoluble hydroxide which settles out as a solid. Carbon sources such as acetic acid, phosphoric acid, hydrochloric acid, sulfonic acid, carboxylic acids, molasses, lactic acid are cited which are disclosed to be used as microbial growth agents. Likewise, nutrients such as nitrogen, phosphorus, and trace elements may be added to support microbial growth if they are deficient in the system. Aqueous residues containing undesirable amounts of Cr(VI) are treated in a continuous bioreactor. Lupton et al. do not disclose the formulation or use of solid-chemical compositions, such as those disclosed in the present invention, which provide for a sustained-release of soluble and insoluble substrates and complex inorganic phosphates. Lupton et al. also do not disclose the application of their method for in-situ remediation, nor do they disclose the application of their process to contaminants other than metals. Hence, Lupton et al. do not disclose the present invention.

U.S. Pat. No. 5,681,739 to Turick et al. discloses a method of reducing the concentration of Cr(VI) in a liquid aqueous residue comprising the steps of providing anaerobic Cr(VI)-reducing bacteria, mixing the liquid aqueous residue with a nutrient medium (e.g., molasses, acetic acid, amino acids, casamino acids, urea), and contacting the mixture with the anaerobic bacteria to enhance the reduction of Cr(VI) to Cr(III). This process can be used for the bioremediation of hexavalent chromium contaminated soil and/or ground water that can be practiced in-situ, ex-situ, or both. The procedure is carried out in an ex-situ bioreactor or in-situ, using the earth as a bioreactor by stimulating indigenous bacteria by adding the nutrient medium directly to the environment. Turick et al. do not disclose the application of their method to contaminants other than metals. Turick et al. do not disclose the formulation or use of solid-chemical compositions, such as those of the present invention, which provide for a sustained-release of soluble and insoluble substrates and complex inorganic phosphates. Hence, Turick et al. do not disclose the present invention.

U.S. Pat. No. 5,582,627 to Yamashita discloses a composition for degrading organic contaminants in soil consisting of a nutrient medium serving as a substrate for microorganisms in the soil (e.g., molasses, mannose, lactose, dextrose, arythrose), a macronutrient component (e.g., ammonia; urea; ammonium salts; nitrates; amino acids; proteins; nucleic acids; phosphoric acid; single, double, and triple superphosphates; salts of phosphoric acid; nitric phosphates; pyrophosphates; nucleic acid phosphates), a micronutrient component (e.g., zinc, iron, manganese), a complexing agent (e.g., lignosulfonates, citric acid, humic acid), and a vitamin/co-factor component (e.g., thiamine, riboflavin, nicotinic acid, pyridoxine, folic acid). The composition is in the form of a liquid and may be applied to the soil through irrigation water or direct spraying onto the soil. Alternatively, the composition may be in the form of a dust or granular material that can be directly mixed into the soil or applied as a suspension in water. Yamashita does not disclose the application of the composition for the treatment of environmental media other than soil or for the treatment of inorganic contaminants. Yamashita does not disclose the formulation or use of solid-chemical compositions, such as those of the present invention, which provide for a sustained-release of soluble and insoluble substrates and complex inorganic phosphates. Hence, Yamashita does not disclose the present invention.

U.S. Pat. No. 5,968,359 to Krahn et al. discloses a method of cleaning up heavy metal-laden soils and water by creating conditions such that microorganisms will form hydrogen sulfide which reacts with heavy metals to form sulfides. According to Krahn et al., by creating hydrogen sulfide, it is possible according to the use of their invention to encapsulate and immobilize heavy metals in the pollution zone. To induce or accelerate the process, a biologically utilizable organic substance is added as a carbon source to ensure anaerobic conditions. Such carbon sources include molasses, acetates, lactates, glycerol, ethanol, and waste from sugar beet production and beer production. Yeast, inorganic nutrients, buffering salts, and sulfur sources are also added to the composition. Krahn et al. do not disclose the application of their method to contaminants other than metals. Krahn et al. do not disclose the formulation or use of solid-chemical compositions, such as those of the present invention, which provide for a sustained-release of soluble and insoluble substrates and complex inorganic phosphates. Hence, Krahn et al. do not disclose the present invention.

Suthersan (U.S. Pat. No. 5,554,290), Nyer and Suthersan (Ground-Water Monitoring Review (GWMR), Summer 1996), and Nyer et al. (GWMR, Spring 1998) teach an in-situ bioremediation process for the creation of what they term "in-situ reactive zones." These reactive zones create an anaerobic environment in the aquifer through the injection of an easily biodegradable carbon source, such as molasses. The injection of molasses causes a rapid increase in the biological activity in the aquifer, thereby consuming the dissolved oxygen and other electron acceptors present in the ground water. A reducing environment is created, whereby Cr(VI) can be removed from solution and precipitated as a chromium hydroxide, nitrates can be anaerobically degraded, and/or chlorinated hydrocarbons can be dehalogenated. The biodegradable carbon source is applied as a dilute aqueous solution. Suthersan (U.S. Pat. No. 5,554,290), Nyer and Suthersan (GWMR, Summer 1996), and Nyer et al. (GWMR, Spring 1998) do not discuss the application of in-situ reactive zones to environmental media other than ground water, nor do they discuss the addition of nutrients to the aqueous solution to promote the growth of contaminant-degrading bacteria. Suthersan (U.S. Pat. No. 5,554,290), Nyer and Suthersan (GWMR, Summer 1996), and Nyer et al. (GWMR, Spring 1998) do not disclose the formulation or use of solid-chemical compositions, such as those of the present invention, which provide for a sustained-release of soluble and insoluble substrates and complex inorganic phosphates. Likewise, they do not disclose the application of the solid-chemical sources of carbon substrates in the preferred forms of granules, briquettes, pellets, tablets and the like. Hence, Suthersan (U.S. Pat. No. 5,554,290), Nyer and Suthersan (GWMR, Summer 1996), and Nyer et al. (GWMR, Spring 1998) do not disclose the present invention.

SUMMARY OF THE INVENTION

In accordance with the present invention, novel solid-chemical compositions are provided for promoting the anaerobic, biologically mediated chemical reduction, biodegradation, transformation, and detoxification of halogenated and hydrophobic organic contaminants and certain inorganic contaminants which may be present in solid and liquid wastes, soils, sediments, water bodies and other environmental media. The principles of this invention provide for a relatively simple and cost-effective means for promoting the anaerobic bioremediation and biologically mediated chemical reduction of such contaminants.

A further object of the invention is to present means by which to overcome the disadvantages associated with not only the traditional methods of remediation previously described but also the limitations of other more recent and/or technically advanced anaerobic bioremediation and chemical-reduction processes described in the prior art. The present invention also provides for significant cost savings relative to other means and methods for environmental remediation. Specifically, the present invention can reduce the operation and maintenance (O&M) costs associated with environmental remediation programs, and it can reduce, if not eliminate, the need for excavation, pumpage, transportation, and/or off-site treatment of contaminated wastes, soil, or water.

The purpose of the present invention is to disclose advanced solid-chemical compositions which provide for a sustained release of organic substrates and complex inorganic phosphates. Specifically, in addition to the complex inorganic phosphates, the solid-chemical compositions of the present invention provide a combination of both water-soluble and insoluble organic substrates, the combined effect of which is to provide both short-lived and long-lived sources of electron donors. Several other beneficial agents may also be included in the solid-chemical compositions of the present invention to enhance the forms and functions of the compositions. These compositions are designed to create, enhance, and maintain anaerobic and reducing conditions which favor anaerobic biodegradation and biologically mediated chemical-reduction processes, e.g., the reductive dehalogenation of halogenated organic contaminants and the reduction of the oxidized forms of inorganic species such as Cr(VI) and U(VI) by anaerobic microorganisms.

The discoveries disclosed herein indicate and/or strongly suggest that many recalcitrant environmental contaminants can be effectively degraded, transformed, and/or detoxifield by indigenous, contaminant-degrading bacteria when the solid-chemical compositions disclosed herein are applied to the contaminated media and the media are subsequently maintained under conditions favorable to the anaerobic microorganisms and the biogeochemical reactions mediated by these organisms, i.e., the media are kept moist or nearly saturated with water These and other objects and advantages of the present invention will become apparent to those skilled in the art following the detailed description of the invention which reveals the novel combination of solid chemical compositions described herein, and more particularly as defined by the claims.

BRIEF DESCRIPTION OF THE FIGURES

FIG. 1 Compares the chlorinated-solvent levels in contaminated soils from an industrial site treated with a liquid-chemical prototype of the solid-chemical composition of the present invention in comparison to the untreated experimental control.

FIG. 2 Illustrates trends in Eh (redox potential) in two ground-water monitor wells at a TCE-contaminated industrial site in response to the application of a preferred embodiment of the solid-chemical composition of the present invention.

DETAILED DESCRIPTION OF THE INVENTION

The present invention discloses unique solid-chemical compositions for the anaerobic bioremediation and biologically mediated chemical reduction of environmental media and wastes contaminated with a broad range of contaminants including halogenated organic compounds (e.g., trichloroethene, tetrachloroethane, freon) and certain inorganic contaminants such as arsenic-based pesticides, cyanides, chromium (VI), uranium (VI) and the oxidized forms of other toxic metals. The disclosed solid-chemical compositions are also believed to have significant potential for the treatment of other hydrophobic, and therefore recalcitrant, organic contaminants, such as organochlorine pesticides, polychlorinated biphenyls (PCFBs) and polycyclic aromatic hydrocarbons (PAHs), by promoting processes which increase the bioavailability and biogeochemical reactivity of such contaminants.

The use as intended of the disclosed solid-chemical compositions and methods provide for a combination of means, mechanisms, processes, and factors which enhance the anaerobic biodegradation, transformation, and detoxification and biologically mediated chemical reduction of recalcitrant environmental contaminants by a wide range of naturally occurring microorganisms including anaerobic bacteria and mycoplasmas, anaerobic fungi and yeasts. The components, formulations and forms of the disclosed solid-chemical compositions are designed to promote and maintain anaerobic and reducing conditions for sufficiently long periods of time in order to enable anaerobic biodegradation and chemical-reduction processes to proceed to the extent that the mass and/or toxicity of the contaminants are reduced to acceptable levels. Based on the information and beliefs of the inventor, bioremediation processes which are expected to be enhanced by the disclosed solid-chemical compositions include the anaerobic biodegradation and biologically mediated chemical reduction of organic contaminants, such as halogenated solvents, organochlorine pesticides and chlorinated hydrocarbons, which are converted into non-hazardous mineral forms and/or less hazardous by-products. In addition, the disclosed solid-chemical compositions are expected to be able to promote the biologically mediated chemical reduction of inorganic contaminants, such as arsenic-based pesticides, cyanides, chromium (VI), uranium (VI) and the oxidized forms of other toxic metals. In addition, the present invention is believed to be capable of promoting the co-precipitation of such inorganic contaminants with mineral species such as sulfides, carbonates, oxides, hydroxides and oxyhydroxides, which may form under the range of Eh–pH conditions created by the application of the disclosed compositions.

In the practice of the present invention, the disclosed solid-chemical compositions would first be prepared in the preferred forms of granules, briquettes, pellets, tablets, or capsules. Next, the disclosed solid-chemical compositions would be applied to and, ideally, mixed into the contaminated wastes (e.g., sludges, solid and/or liquid wastes, and the like) or other contaminated media such as soils, sediments, or water bodies, and the like. For applications involving the treatment of contaminated ground waters and aquifer media, these preferred forms of the solid-chemical compositions (e.g., granules) would be applied in filter socks, canisters, or cartridges within wells installed in the contaminated areas. Such applications of the disclosed solid-chemical compositions provide numerous advantages over bioremediation methods which involve the use of liquid-chemical compositions, including the reduction, if not elimination, of much of the equipment and labor required to operate and maintain an effective remediation program.

A critical advantage of the disclosed solid-chemical compositions of the present invention is that they provide a balanced source of soluble and insoluble organic substrates in highly concentrated, solid forms which enable extremely high concentration gradients to be established when applied to the environmental media being treated. The solid-chemical compositions disclosed herein are comprised of at least three components as follows.

(1) soluble organic substrates; and (2) substantially insoluble organic substrates; and (3) complex inorganic phosphates A particular advantage of the combination of (1) soluble substrates and (2) substantially insoluble organic substrates is to provide substrates in forms which both (1) quickly disperse and diffuse into environmental media and (2) are slowly biodegraded over time. This combination of substrates provides for both (1) a rapid initial flux of electron donors into the contaminated media and (2) a sustained-release of electron donors over time. The complex inorganic phosphates provide nutrient phosphorus in forms which are less geochemically reactive in environmental media than are simple organic phosphates and which provide a milder level of surfactant activity. These complex inorganic phosphates also serve to inhibit aqueous corrosion and precipitation reactions, such that in the present invention they also help to minimize the formation of undesirable precipitates when the compositions are applied to environmental media.

For purposes of explanation, and not limitation, the inventor's use of the term "soluble organic substrates" is meant to imply such organic substrates that have a substantially high degree of solubility in cool water, such as the 45° F. to 65° F. temperature range of most ground waters. By contrast, the inventor's use of the term "substantially insoluble organic substrates" is meant to imply such organic substrates that have a substantial lack of solubility in cool water, such as the 45° F. to 65° F. temperature range of most ground waters.

In the preferred embodiments of the present invention, the soluble organic substrates included in the disclosed solid-chemical compositions would be selected from one or more of the following:

(1a) soluble sugars, molasses, and milk;

(1b) soluble organic salts;

(1c) soluble organic polymers

Additional components which may be included in the disclosed solid-chemical compositions include organic and inorganic sources of nitrogen; simple phosphates; chelating agents; disintegrants; fillers, binders and pH buffers; lubricants and glidants; plant-material and organic-polymer degrading enzymes; and inoculum for different types of microorganisms, including microorganisms which produce the aforementioned plant-material and organic-polymer degrading enzymes.

The novel combinations of ingredients in the disclosed solid-chemical compositions provide for a well-balanced, sustained-release source of biodegradable organic substrates and complex inorganic phosphates, which in turn provide improved means of stimulating and maintaining conditions favorable for the anaerobic bioremediation and biologically mediated chemical-reduction of persistent environmental contaminants.

In the present invention, a source of soluble organic substrates (1) is provided in the solid-chemical compositions. In the preferred embodiments of the present invention, the soluble organic substrates would preferably be selected from one or more of (1a) soluble sugars, molasses, and milk; (1b) soluble organic salts; and (1c) soluble organic polymers. In the preferred embodiments of the present invention, the soluble organic substrates would include one or more selected from the group consisting of powdered and granulated white, brown and organic sugars; powdered and granulated corn sugars; powdered and granulated whole milk and low-fat milk; powdered and granulated molasses; powdered and granulated mannose, glucose, galactose, lactose, dextrose, xylose and arythrose; and powdered and granulated grain-malt extracts. In one of the preferred embodiments of the present invention recently tested by the inventor, component (1a) included a mixture of powdered molasses, granulated organic brown sugar and powdered low-fat milk. The recent research of the inventor suggests that the inclusion of the other soluble sugar- and milk-containing substrates listed above may be advantageous as they may help promote the growth of a more diverse microbiological community in contaminated environmental media.

The primary advantage of the inclusion of the aforementioned source of the soluble sugars, molasses, and milk is to provide a concentrated source of highly soluble electron donors which diffuse relatively quickly into environmental media. Another advantage of the inclusion of these sources of soluble sugars, molasses and milk in the disclosed compositions is to promote rapid and robust microbiological activity, including liquid-substrate fermentation processes, which help consume the available oxygen supply and create anaerobic and reducing conditions in contaminated environmental media. The relatively high solubilities of these substrates enables very-high concentration gradients to be established when the disclosed compositions are applied to contaminated environmental media and wastes, which provides a means for establishing the rapid flux of these substrates into such media via molecular diffusion and dispersion processes. Given that advective solute transport rates are inherently limited by the permeability of the media being treated, this advantage of the present invention provides an important means of overcoming these limitations, thereby increasing the speed and effectiveness of environmental remediation via anaerobic bioremediation and chemical-reduction processes.

Another important reason for the inclusion of these soluble sources of sugars, molasses and milk as a subcomponent of the soluble organic substrates in the disclosed compositions is to stimulate liquid-substrate fermentation processes which produce beneficial byproducts which are either impractical or more expensive to include in the solid-chemical composition, such as alcohols, esters, acetates and organic acids. These fermentation products in turn help promote the activity of a more diverse range of anaerobic microorganisms which is believed to help provide for more effective and complete environmental remediation. Moreover, certain fermentation products, such as alcohols and the somewhat less-desirable ketones, are highly soluble and biodegradable organic solvents which can help increase the bioavailability of hydrophobic organic contaminants, such as chlorinated solvents, thereby enhancing the aforementioned bioremediation processes.

The soluble organic salts (1b) which may be included in the disclosed compositions would preferably be selected from one or more soluble salts of fatty acids, such as lactates, formates, acetates, sorbates, and citrates. In the preferred embodiments of the present invention, the source of organic salts would be further selected from one or more of the group consisting of calcium lactate, magnesium lactate, sodium formate, potassium formate, sodium acetate, calcium acetate, potassium acetate, sodium sorbate, potassium sorbate, sodium citrate, potassium citrate, citric acid, and any combinations thereof. These soluble organic salts provide another complimentary source of highly-soluble organic substrates which can rapidly diffuse and disperse into environmental media. These soluble organic salts of fatty acids are also among the most preferred "labile" substrates for anaerobic, metal-reducing bacteria, which are believed to be an important segment of the naturally occurring, contaminant-degrading bacteria in the environment. Hence, it is the inventor's belief that the inclusion of such soluble organic salts in the disclosed solid-chemical compositions can enhance the aforementioned bioremediation processes by promoting the growth of a more diverse consortia of microorganisms in contaminated environmental media.

The soluble organic polymers (1c) which may be included in the solid-chemical compositions of the present invention are preferably selected from one or more of the group consisting of soluble starches, soluble cellulosic compounds and soluble gums. In the preferred embodiments of the disclosed compositions of the present invention, the soluble starches are selected from one or more of the group consisting of soluble corn starches, soluble tapioca starchs, soluble grain and potato starches, and other soluble starches. The soluble cellulosic materials are preferably selected from the group consisting of sodium carboxymethyl cellulose, hydroxypropyl cellulose and other soluble cellulosic compounds. The soluble gums are preferably selected from one or more of the group consisting of gum arabic, guar gum, carboxymethyl guar gum, hydroxypropyl guar gum, and xanthan gum; carageenan; and alginate salts, which being refined sources of macroalgal algin, provide algin in highly soluble, solid-chemical forms such as sodium alginate, potassium alginate, ammonium alginate, ammonium-calcium alginate and sodium-calcium alginate.

A specific advantage of the inclusion of such soluble organic polymers (1c) in the solid-chemical compositions disclosed herein is that they provide a source of organic substrates which disperse less quickly and are longer lived in the environment than the highly soluble organic substrates described in (1a) and (1b). By contrast, these soluble organic polymers provide a source of substrates which disperse more quickly and are shorter-lived than the insoluble substrates described in (2). Accordingly, the inclusion of such soluble organic polymers (1c) in the disclosed compositions of the present invention provides a source of intermediate-lived organic substrates which bridges the gap between the most labile organic substrates, (1a) and (1b), and the comparatively long-lived insoluble organic substrates, (2). The technical basis for the preferred use of soluble starches, soluble cellulosic materials and soluble gums in (1c) lies in the fact that these organic polymers are broken down by specific microbial and fungal enzymes into their constituent building blocks, namely sugars and organic acids. Hence, another intended function of these soluble organic polymers in the present invention is to provide an intermediate-lived, sustained-release source of the sugars and organic acids stored in these organic polymers. It is the inventor's belief that the inclusion of such intermediate-lived substrates in the disclosed solid-chemical compositions of the present invention can help promote the growth of a more diverse community of beneficial microorganisms within contaminated environmental media.

The substantially insoluble organic substrates (2) included in solid-chemical compositions of the present invention would preferably be selected from one or more of the group consisting of legume-derived plant materials, rice, cotton lint, recycled cotton fibers and other sources of fibrous, plant-derived materials; recycled paper and cardboard; cellulose powder, microcrystalline cellulose, and other insoluble cellulosic materials; lignocellulose, sawdust, kenaf and other sources of lignocellulose; insoluble forms of lignin, pectin and chitin and other organic and/or plant-derived materials containing insoluble forms of lignin, pectin and chitin; insoluble grain and vegetable starches and pre-gelled starches; insoluble grain and vegetable flours; agar, karaya gum, locust-bean gum and other substantially insoluble gums; and any combinations thereof. In the preferred embodiments of the present invention, at least some, if not most, of the insoluble organic substrates are provided in the forms of cellulose powder, powdered insoluble starches, pre-gelled starches and flours derived from grains and vegetables and fibrous plant materials derived from legumes.

The specific advantages of the inclusion of such insoluble organic substrates (2) in the disclosed solid-chemical compositions is to provide a source of organic substrates which are relatively long-lived in the environment and which slowly disperse as they are biodegraded over time. The technical basis for the preferred use of substantially insoluble cellulosic materials, plant materials, starches and gums in (2) is similar to that described above for the soluble organic polymers (1c) and stems from the fact that specific microbial enzymatic processes break down these insoluble organic materials and polymers into their constituent building blocks, e.g., sugars. Hence, the intended function of such insoluble substrates in the present invention is to provide a long term, sustained-release source of organic substrates and the component sugars contained in these materials.

The complex inorganic phosphates included in the disclosed solid-chemical compositions would be selected from any number of ringed metaphosphates and linear polyphosphates. In the preferred embodiments of the present invention, the complex inorganic phosphates would be further selected from one or more of the group consisting of sodium hexametaphosphate, sodium trimetaphosphate, sodium tripolyphosphate, sodium-potassium tripolyphosphate and tetrasodium pyrophosphate. Such complex inorganic phosphates provide sources of nutrient phosphorus in forms which are enzymatically hydrolyzable by microorganisms and which are relatively non-reactive geochemically. Hence, the inclusion of these complex phosphates in the disclosed solid-chemical compositions enables the more effective and efficient delivery of nutrient phosphorus to biological organisms and microorganisms in contaminated environmental media. In the forms of the present invention recently tested by the inventor, at least some if not all of the complex inorganic phosphates have been supplied in the form of sodium hexametaphosphate and sodium trimetaphosphate.

An organic source of nitrogen may also be included in the solid-chemical compositions. The organic source of nitrogen is preferably selected from materials derived from the plant families Leguminosae and Phaeophyta, and any combinations thereof. In the preferred embodiments of the present invention, the source of organic nitrogen is further selected from plant materials derived from Lespedeza spp., Medicago spp. (e.g., alfalfa), Vicia spp. (e.g., vetches), Glycine spp. (e.g., soy), Lathyrus spp., Trifolium spp. (e.g., clovers), Sargassum spp., and any combinations thereof. These plant materials contain relatively large amounts of nitrogen in various forms including proteins and electron-acceptor species of nitrogen. The main advantage of the organic source of nitrogen is that it provides a source of nutrient and/or electron acceptor nitrogen in a biodegradable, organic form which is highly compatible with the other components of the disclosed solid-chemical compositions. Moreover, these plant-derived forms of organic nitrogen provide for sustained release of nitrogen which provides a means of meeting the prolonged biological demand for nitrogen created by the sustained release of the organic substrates in the disclosed compositions of the present invention.

A source of inorganic nitrogen may also be included in the solid-chemical compositions in order to provide a supplemental source of nitrogen as a nutrient, electron acceptor or both. In the preferred embodiments of the present invention, the source of inorganic nitrogen would be selected from ammonium-free nitrate salts such as sodium nitrate, sodium-potassium nitrate, and potassium nitrate. A specific advantage of the use of ammonium-free, inorganic nitrate salts is to provide nitrate nitrogen which can serve as both an electron acceptor for denitrifying microorganisms and as an inorganic form of nutrient nitrogen.

A source of simple inorganic phosphates may also be included in the disclosed solid-chemical composition. In the preferred embodiment of the present invention, the simple inorganic phosphates would be selected from one or more of the group which includes sodium phosphate, calcium phosphate, potassium phosphate, and sodium-potassium phosphate. These simple inorganic orthophosphates not only can provide additional sources of nutrient phosphorus for microorganisms, but they also can serve as surfactants to enhance the solubility and bioavailability of hydrophobic organic contaminants.

The aforementioned simple orthophosphates can also help serve as release-rate modifiers for some of the other soluble components in the disclosed compositions. For example, by combining the use of calcium phosphate with the aforementioned gums in the present invention, (soluble gums, insoluble gums or both), gels of different viscosities can be made to form within the matrix of the solid-chemical compositions after they are placed in contact with water. Hence, the release rate profiles of the soluble organic substrates and complex phosphates can be modified by controlling the composition and viscosity of such gels, which may be highly advantageous for certain environmental-remediation applications. It is the inventor's belief that this aspect of the present invention can also provide a means for achieving longer and steadier sustained-release profiles of the various substrates and complex phosphates included in the compositions.

A source of chelating agents may also be included in the disclosed solid-chemical compositions of the present invention. In the preferred embodiments of the present invention, these chelating agents would be selected from one or more of the group comprising citric acid, humic acid, fulvic acid, potassium citrate, sodium citrate, nitrilotriacetic acid (NTA) and ethylenediaminetetraacetic acid (EDTA). The inclusion of such chelating agents can be used to help promote anaerobic microbiological processes coupled to the reduction of various metals, such as iron (III), chromium (VI) and uranium (VI), as well as the use of various metals as micronutrients by microorganisms. In the present invention, the use of citric acid and sodium citrate are the preferred chelating agents, as they are both effective chelators and organic substrates. The use of potassium citrate and humic and fulvic acids provides for similar and complimentary benefits to the use of citric acid and sodium citrate.

A source of fillers, binders and pH-buffers, and any combination thereof, may also be included in the solid-chemical compositions of the present invention. In the preferred embodiments of the present invention, the fillers, binders and pH-buffers would be selected from one or more of the group consisting of waxes, calcium carbonate, lime, limestone, siderite and ferrous carbonate, rhodochrosite and manganese carbonate, calcium phosphate, sodium bicarbonate, portland cement, metal oxides, metal hydroxides, metal oxyhydroxides, and any combinations thereof. Depending on the forms and formulations of the different substrates included in the disclosed solid-chemical compositions, these fillers, binders and pH-buffer can enable a wider range of formulations to be manufactured in the preferred forms of granules, briquettes, tablets, pellets and the like. These fillers, binders and pH-buffers can also be used to help extend the sustained-release profiles of the "active" ingredients in the disclosed composition by slowing the rates of disintegration of the preferred forms of the compositions (e.g., granules, briquettes), as well as by slowing the dissolution rates of the active ingredients from these manufactured forms of the composition. Furthermore, these fillers, binders and pH-buffers can also help improve the storage and handling characteristics of the preferred forms of the compositions (e.g., briquettes, granules) by enabling the hardness and compaction of these forms to be increased, thereby reducing the amount of nuisance dusts produced by handling such forms.

Depending on the specific application and/or the desired sustained-release profiles of the substrates, complex phosphates and other amendments included in the disclosed solid-chemical compositions, a source of disintegrants may also be used in the compositions. The disintegrants would preferably be selected from one or more of the group consisting of pre-gelled starch, sodium starch glycolate, crosscarmelose of sodium, crospovidone, and any combinations thereof. In contrast to the aforementioned binders and fillers, the use of such disintegrants would enhance the disintegration of the preferred forms of the disclosed solid-chemical composition e.g., granules, briquettes, pellets, tablets, and the like, and thereby increase the rates of dissolution and dispersion of the substrates, complex phosphates and other amendments. Noteworthy is that the aforementioned preferred disintegrants are in and of themselves biodegradable organic substrates, such that in addition to their function as disintegrants, they are compatible with and complimentary to the other organic substrates included in the disclosed solid-chemical compositions.

A source of lubricants and glidants may also be included in the disclosed solid-chemical compositions of the present invention. The lubricants and glidants would preferably be selected from one or more of the group consisting of magnesium stearate, calcium stearate and other stearates, stearic acid, sodium stearyl fumarate, hydrogenated vegetable oil, corn starch, and any combinations thereof. These lubricants and glidants are particularly useful manufacturing aids for the preparation of the preferred forms of the compositions (e.g., granules, briquettes) in that they increase the manufacturing efficiency by decreasing the degree to which the composition may stick or adhere to various components of the manufacturing equipment. For example, the inventor has found that the inclusion of as little as about 0.5% of magnesium stearate in several different embodiments of the disclosed solid-chemical compositions greatly improved the quality and rate-of-production of these compositions in the forms of briquettes and granules. Again, it should be noted that the aforementioned preferred lubricants and glidants are in and of themselves biodegradable organic substrates, such that in addition to their primary functions as lubricants and glidants, they are compatible with and complimentary to the other organic substrates included in the disclosed solid-chemical compositions.

A source of inoculum for biological organisms and microorganisms may also be included in the disclosed solid-chemical compositions. The source of inoculum would be selected from one or more of the group consisting of anaerobic bacteria, facultative bacteria and other bacteria capable of utilizing terminal electron acceptors other than oxygen; mycoplasmas; anaerobic fungi; yeasts; and any combinations thereof. In the preferred embodiments of the present invention, the source of inoculum would be further selected from the group consisting of yellow boy (a byproduct of acid mine drainage believed by the inventor to be a source of inoculum for both metal-reducing and metal-oxidizing microorganisms), Bacillus spp., Rhizobium spp., Bradyrhizobium spp., Fibrobacter spp., Clostridium spp. Pseudomonas spp., Geobacterspp., Arthrobacterspp., Nocardia spp., Aspergillus spp., Trichoderma spp., Candida spp., Yarrowia spp., and any combinations thereof. These inoculum may include soil microorganisms (e.g., Pseudomonas spp.), nitrogen-fixing microorganisms (e.g., Rhizobium spp., Bradyrhizobium spp.), metal-reducing microorganisms (e.g., Geobacterspp.), fungi (e.g., Aspergillus spp.) and yeasts (e.g., Candida spp., Yarrowia spp.). The main purpose of the inclusion of inoculum for such a diverse range of microorganisms and fungi is to help promote a variety of microbiological and biogeochemical processes which serve to directly or indirectly enhance the ability of the present invention to stimulate the aforementioned anaerobic bioremediation and biologically mediated chemical-reduction processes. Another, broader function provided for by the inclusion of these inoculum in the present invention is to add "bioaugmentation" to the spectrum of functions provided for by the disclosed solid-chemical compositions—i.e., the addition of beneficial, non-indigenous microorganisms to the contaminated environmental media. The bioaugmentation function of the inoculum in the disclosed compositions may be advantageous for applications which involve the treatment of unusual or highly-concentrated waste streams. This bioaugmentation functionality may also be useful to help establish populations of beneficial microorganisms in harsh environments and environments which may have been partially "sterilized" by prior treatments with strong oxidizers or anti-microbial agents, or by the presence of other agents which are toxic to microorganisms. A specific example of an application where such bioaugmentation-related benefits of the present invention would be beneficial, if not warranted, would be at contaminated sites which had previously undergone unsuccessful chemical-oxidation treatment with such oxidizing agents as potassium permanganate, hydrogen peroxide and other peroxygen compounds.

A source of organic polymer and plant-material degrading enzymes may also be included in the disclosed solid-chemical compositions. In the preferred embodiments of the present invention, the source of enzymes would be further selected from one or more of the group consisting of cellulases, hemicellulases, lignocellulases, amylases, glucanases, proteases, chitinases, lipases, and any combinations thereof. The primary purpose of the incorporation of such specific enzymes is to enhance the degradation of the various organic polymers and plant derived materials included in the present invention into their constituent "building blocks," e.g., sugars and fatty acids. Another, related function of these enzymes is to provide additional means for controlling the release-rate profiles of the substantially insoluble organic substrates and soluble organic polymers included in the compositions.

In addition to and/or in lieu of the incorporation of organic polymer and plant-material degrading enzymes in the present invention, a source of inoculum for microorganisms which produce such organic polymer and plant-material degrading enzymes may also be included in the disclosed solid-chemical compositions. In the preferred embodiments of the present invention, this source of inoculum is further selected from microorganisms which produce one or more of the following enzymes which include cellulases, hemicellulases, lignocellulases, amylases, glucanases, proteases, chitinases, lipases, and any combinations thereof. As for the inclusion of the enzymes themselves, the primary purpose of the incorporation of microbial inoculum which produce these enzymes is to aid the degradation of the soluble and substantially insoluble organic polymers and plant derived materials included in the compositions into their constituent "building blocks," e.g., sugars and fatty acids. Another, related function of these enzyme-producing microorganisms is to provide another means for controlling the release-rate profiles of the substantially insoluble organic substrates and soluble organic polymers included in the disclosed solid-chemical compositions.

Advantages of the use of such specific microbial inoculum in the present invention include reducing the cost and increasing the shelf-life of the intended byproducts of these inoculum—i.e., the organic polymer and plant-material degrading enzymes. In the preferred embodiments of the present invention, particular emphasis is placed on the use of inoclum for plant-fiber degrading microorganisms such as the anaerobic bacteria Fibrobacter spp., Clostridium spp., and the like and/or plant-fiber degrading species of fungi, as well as microorganisms which produce plant fiber and organic substrate degrading enzymes such as Arthrobacter spp., Nocardia spp., Bacillus spp., Aspergillus spp., and Trichoderma spp. The inclusion of inoculum of such biota provides a means for establishing adequate populations of these organisms in relatively challenging, difficult or otherwise unusual environmental remediation applications such as the bioremediation of industrial or hazardous wastes, waste lagoons, natural bodies of water (e.g., oceans, rivers, lakes, streams, and the like), or deep sediments or rock formations where such microorganisms may not normally be present in sufficient abundance.

A particular advantage of the present invention is the release-rate profiles of the substrates contained in the disclosed solid-chemical compositions can be varied as a function of, both (i) the proportions of the total soluble organic substrates to the total substantially insoluble organic substrates in the compositions, and (ii) the formulation of the actual sub-components of the soluble and insoluble substrates. For example, a more aggressive and rapid substrate-release-rate profile can be facilitated by incorporating not only a relatively high proportion of soluble organic substrates in the composition (e.g., 70%–90+%), but also a relatively high proportion of (a) soluble sugars, molasses, milk and (b) soluble organic salts. By comparison, gentler and longer substrate-release-rate profiles can be provided by incorporating a relatively high proportion of substantially insoluble organic substrates in the composition (e.g., 50%–90+%), as well as by using lower proportions of (a) sugars, molasses, milk and (b) soluble organic salts in the formulation of the soluble organic substrate component of the composition. Alternatively, a different and complimentary means of varying the substrate-release rate profiles is to use relatively high proportions (>5–10%) of soluble organic polymers, such as gums, either alone or in combination with gel-setting agents such as calcium carbonate, calcium phosphate, and other agents, to promote the formation of gels in the matrix of the compositions after they have been exposed to water. By varying the composition, viscosity and/or strength of these gels, another means of varying the substrate-release rate profiles is provided in the present invention. Examples of the effects of such variables on the sustained-release profiles of various embodiments of the disclosed solid-chemical compositions is provided below.

The disclosed solid-chemical compositions of the present invention would preferably be prepared into the forms of granules, briquettes, pellets, tablets, and capsules which are significantly easier to store, handle and use than the powdered forms of the disclosed compositions as well as the powdered and liquid forms of other compositions. These preferred forms of the solid-chemical compositions can be readily and economically produced using available manufacturing equipment and processes utilized by the pharmaceutical, neutraceutical, specialty chemical and animal-feed industries.

An important advantage of the preferred granule, briquette, pellet, capsule, and/or tablet forms of the disclosed composition is that they are easier to store, handle, and use than other forms of the disclosed composition, as well as other compositions provided in the forms of powders and liquids. For example, these forms of the disclosed compositions produce less dust when handled, they can be handled and applied using mechanized equipment, and they can be used under adverse field conditions—e.g., windy conditions. These forms of the present invention also prevent the segregation or settling out of one or more constituents included in the disclosed solid-chemical compositions—this enables a greater range of formulations to be practically and reliably prepared and a wider range of environmental remediation applications to be undertaken using the present invention. These preferred forms of the present invention also provide for a greater shelf life of the solid-chemical compositions owing to the reduction in surface area (in comparison to a powder).

In addition, these preferred forms of the invention provide end users with a simple and inexpensive means of conducting routine operation and maintenance (O&M) of bioremediation programs by enabling them to "refill" application devices such as filter socks and canister systems on their own, such as would be advantageous for ground-water remediation programs. These preferred forms of the disclosed solid-chemical compositions can be provided to end users both in bulk and in "kit" form to reduce the costs and simplify the logistics of site remediation O&M. These preferred forms of the invention also provide means for facilitating and controlling a delayed, time-release type of interaction between the composition and the contaminated media—consequently these forms provide another means of controlling the sustained-release profiles of the various amendments incorporated into the compositions to help meet the project- or site-specific requirements of the end user.

Another advantage of the preferred granule, briquette, pellet, capsule, or tablet forms of the present invention is that the final specific gravity of these forms can be "engineered" such that they rapidly sink in water. Hence, these forms of the disclosed solid-chemical compositions provide the means by which to apply the composition to the remediation of more complicated contamination problems, such as in the bioremediation of contaminated sediments in-situ beneath natural waters (e.g., oceans, lakes, rivers, streams, and the like) and man-made water bodies (e.g., waste-treatment lagoons and the like) and the remediation of dense non-aqueous phase liquids (DNAPLs) and/or depth-specific stratigraphic layers present in subsurface hydrogeologic environments. For example, if it can be determined that high levels of contaminants are trapped in specific strata or at specific depths, such as is often the case with DNAPL solvents such as TCE and PCE, the rapid-sinking nature of the granulated compositions provides a means for targeting the treatment of such contamination. In addition, for applications involving the in-situ bioremediation of contaminated bedrock aquifers, these forms can be poured directly into "open rock" wells or boreholes in the rock, providing for a simple and inexpensive means of conducting repeated applications of the disclosed compositions.

As described above, the solid-chemical compositions of the present invention disclosed herein provide for unique advantages, means, and methods of achieving the relatively rapid and effective chemical reduction and anaerobic bioremediation of recalcitrant organic and inorganic contaminants present in wastes, soils, waters, or sediments versus the means and methods disclosed in the prior art. The solid-chemical compositions disclosed herein and the means and methods for their intended use overcome many of the disadvantages associated with traditional remediation methods by providing for the efficient and cost-effective remediation of environmental contaminants on a commercial scale with minimal disturbance to the contaminated area. The solid-chemical compositions disclosed herein and the means and methods for their intended use also overcome many of the disadvantages associated with the more advanced means and methods for the chemical and biological remediation of environmental contaminants disclosed in the prior art.

EXAMPLES

The following examples are provided to illustrate the technical basis, merits and unique advantages provided by the present invention. These examples are not to be construed as limiting the present invention in any way, but are merely presented as examples of the unique advantages and non-obvious improvements of the present invention over the prior art and to illustrate the practice of the present invention as described in the appended claims.

Example 1

Bench-scale experiments were conducted to evaluate the effectiveness of the application of several liquid-chemical compositions to fine-grained soils contaminated with a mixture of chlorinated solvents and hydrocarbons from a contaminated industrial site. The most effective liquid-chemical composition, a prototype of the present invention, reduced the total levels of chlorinated solvent compounds by as much as 96% relative to the experimental control and baseline samples. This prototype composition included a combination of molasses, granulated organic brown sugar, sodium carboxymethyl cellulose and sodium hexametaphosphate.

Noteworthy was that the contaminated soils treated with the prototype composition comprised a very-low permeability, putty-like silty clay; hence, the diffusion-driven flux of the substrates and amendments included in the prototype composition was believed to have been an important factor in the success of these experiments. Concentrations of total chlorinated compounds in the control and pre-treatment samples ranged from 6 mg/Kg to 40 mg/Kg, whereas concentrations of individual compounds ranged from 1.4 mg/Kg to 3.6 mg/Kg of PCE, 1.6 mg/Kg to 3.3 mg/Kg of TCE, and from <1 mg/Kg to 35 mg/Kg cis-1,2-DCE. Two months after treatment with the prototype composition, PCE was completely removed, TCE levels were reduced by 85–100% and cis-1,2-DCE levels were reduced by 65–100%. In addition total mass of organic compounds measured in the soils, which are comprised of mostly of relatively high-molecular weight polycyclic aromatic hydrocarbons (PAHs), was reduced by up to 28%. PAHs are typically quite hydrophobic and have a very limited degree of bioavailabilty with respect to microorganisms; hence, PAHs and relatively recalcitrant in the environment. Therefore, these indications of reductions in PAH mass suggests that the prototype composition was able to increase the bioavailability of the PAHs, and consequently, the rate of PAH biodegradation.

Example 2

The inventor has successfully manufactured granulated and briquetted forms of a number of different embodiments of the disclosed solid-chemical compositions of the present invention using a Fitzpatrick Model IR 520 Chilsonator System, including a Model M5A granulator. The Model IR 520 Fitzpatrick Chilsonator system is a small-scale version of larger Fitzpatrick briquetting and granulation systems, and is typically used for small-scale production runs and prototype tests, the results of which can be scaled to larger Fitzpatrick Chilsonator systems.

The briquetted and granulated embodiments of the present invention which were successfully produced with the Fitzpatrick Chilsonator system included the solid-chemical compositions designated as the "3" through "8" series "substrate-release compositions" or "SRC." The embodiments of the present invention produced with the Fitzpatrick Chilsonator system included a broad range of the formulated proportions of the soluble organic substrates and substantially insoluble organic substrates in the compositions, and a lesser degree of variation in the formulation and proportions of the inorganic phosphates and other amendments incorporated in the compositions. Each of the granulated embodiments of the solid-chemical compositions produced with the Fitzpatrick Chilsonator system included a combination of significant amounts of soluble organic substrates (<30%–90% by weight) and substantially insoluble organic substrates (10%–70% by weight), lesser amounts of complex inorganic phosphates (<2%–7% by weight) and small amounts of organic-polymer-degrading enzymes and microbial inoculum which produce such enzymes (<0.5%). For example, the "SR-3.1" composition included approximately 70%, by weight, of substantially insoluble organic substrates, including cellulose powder, grain starch powder and alfalfa meal; 27% soluble substrates comprised of mostly powdered molasses and sodium carboxymethyl cellulose; and 2.5% complex inorganic phosphates in the form of sodium hexametaphosphate. By comparison, the "SRC-4.2" composition included only 10%, by weight, of substantially insoluble organic substrates, including cellulose powder, grain starch powder and alfalfa meal; nearly 90% soluble organic substrates comprised of granulated organic brown sugar, powdered molasses and sodium carboxymethyl cellulose; and approximately 5% complex inorganic phosphates, including sodium hexametaphosphate, sodium trimetaphosphate and tetrasoidium pyrophosphate. A number of other formulations of the disclosed solid-chemical compositions, including the "SRC-5," "SRC-6" and "SRC-8" series compositions and several different embodiments of the "SRC-7" series compositions were successfully manufactured as well; these compositions contained varying levels of soluble and insoluble organic substrates and complex phosphates in the intermediate ranges between the "3" and "4" series compositions described above. Noteworthy is that the "SRC-7" series compositions successfully introduced additional sources of soluble substrates including soluble organic salts (e.g., sodium formate), and powdered low-fat milk. In general, the briquettes and granules of these different embodiments which were produced with the Fitzpatrick Chilsonator system were of good quality such that they could be readily handled with minimal dusting and breakage.

Several preferred embodiments of the compositions, such as the "SRC-7" series of compositions and the "SRC-4.2" composition, introduced magnesium stearate as a biodegradable lubricant and glidant, which was observed to improve the degree of compaction of the granules, and, importantly, their rates of production with the Fitzpatrick Chilsonator system. The results of the production testing of these compositions indicates that the inclusion of less than 1% magnesium stearate in these compositions by weight can significantly enhance the production efficiency of the granulated compositions using the Fitzpatrick Chilsonator system, such that these and other embodiments of the present invention can be readily scaled to large-scale production. Moreover, based on the results of the production-testing of these various embodiments of the present invention with the Fitzpatrick Chilsonator system, it is the inventor's belief that a much broader range of components and formulations of the solid-chemical compositions can be successfully produced as disclosed herein.

From the perspective of the preparation of the aforementioned granular embodiments of the disclosed compositions, the use of the Fitzpatrick Chilsonator systems is advantageous in that they are self-contained systems which are designed to minimize the production of dusts. As the original forms of many of the components of these granulated forms of the disclosed compositions are finely divided organic powders, the minimization and pro-active control of fugitive dust emissions is an important and necessary industrial safety measure. These and other material-handling and quality-control advantages of the Fitzpatrick Chilsdnator systems appear to be why they are widely used in the pharmaceutical and neutraceutical industries, and hence, why they are a preferred means of producing the solid-chemical compositions of the present invention.

Example 3

A field-scale demonstration was initiated in September 2000 to test the application of a combination of three different, preferred embodiments of the solid-chemical compositions disclosed herein to treat chlorinated solvents present in ground-water at an industrial site. These embodiments were designated as the "SRC-4," "SRC-5" and "SRC-6" series compositions. Each of the three preferred embodiments of the disclosed compositions was prepared in granular form using the Fitzpatrick Model IR 520 Chilsonator System, including a Model M5A granulator. Each of the compositions included different proportions of soluble and insoluble organic substrates, and included different combinations of powdered molasses, granulated organic brown sugar, citric acid, sodium carboxymethyl cellulose, cellulose powder, powdered insoluble starch/flour, alfalfa meal, and complex inorganic phosphates (primarily comprised of sodium hexametaphosphate).

On Sep. 28, 2000, 10 lbs. of each of the three granulated compositions were applied in filter socks below the water table in a 4-in. diameter well, MW-1S, which had previously been installed in an unconsolidated geologic formation comprised of fine-silty sands of coastal marine-estuarine origin. Prior to the addition of the composition, the Eh (redox potential) measured in the well was +57.1 millivolts (mv). As shown in FIG. 2, thirty three days after treatment, the Eh in MW-1S decreased to −116.7 mv, whereas by sixty-three days after treatment, the Eh dropped further to −119.8 mv. Dissolved oxygen (DO) levels in MW-1S decreased slightly from 0.45 mg/l in September 2000 to 0.35 mg/l in November 2000. These observations confirmed the capability of the composition to create and maintain reducing conditions in-situ, which, as documented in the literature, are known to favor anaerobic dechlorination processes. Field observations also indicated robust biological activity in the well.

The organic-compound monitoring data showed an increase in trichloroethene (TCE) levels and a slight increase in the relative proportion of biodegradation "daughter" products of TCE as of 63 days after the application of the solid-chemical composition of the present invention. TCE levels in well MW-1S rose from 500 µg/l, observed in June 2000, and 57 µg/l, observed in September 2000, to 810 µg/l in November 2000, 63 days after application of the composition in MW-1S. Such observations of an initial increase in dissolved-phase contaminant levels have commonly been observed in successful in-situ ground-water bioremediation programs. The inventor's hypothesis, which is consistent with the view of others in the scientific community, is that these observations are attributable to the enhanced solubility and desorption of these particle-reactive compounds from the subsurface media in response to the increased biological activity (e.g., such as that caused by the addition of the composition). Specific factors which may have contributed to these observations of increased contaminant solubility include the production of "biosurfactants" and organic solvents by microorganisms in response to the application of the disclosed solid-chemical composition to site ground water. As do others knowledgeable in the art, the inventor considers the stimulation of such processes critical to the long-term, overall success of in-situ bioremediation programs.

Noteworthy was the documentation in December 2000 of the presence of elevated levels of several desirable fermentation byproducts in the ground-water produced by the application of the composition—ethyl and butyl acetates and alcohols. Also noteworthy was the absence of less desirable fermentation byproducts in the treated ground water, such as ketones. Ethyl and butyl acetates and alcohols are highly biodegradable compounds produced by the microbial fermentation of the substrates provided in the composition. Hence, these data indicate that the solid-chemical composition of the present invention successfully stimulated the desired acetate/alcohol fermentation pathways versus the less desirable ketone-producing pathways. The subsequent production of the ethyl and butyl alcohols after the application of the disclosed solid-chemical compositions is an important advantage of the present invention as these compounds are highly soluble and biodegradable solvents which can help increase the bioavailability of the chlorinated solvents, thereby enhancing bioremediation. Accordingly, the alcohols produced by the fermentation of the composition are believed to be at least partially responsible for the initial increase in chlorinated solvent levels observed in response to the application of the composition.

Also noteworthy was that the different compositions exhibited different substrate release-rate profiles, as intended. For example, the "SRC-6" composition, which contained the highest proportion of substantially insoluble organic substrates (approximately 30%) and the lowest proportion of soluble substrates (approximately 60%), showed the least weight loss over the two-month observation period and appeared to provide for the longest and gentlest substrate-release profile. By comparison, the "SRC-4" composition, which contained the lowest proportion of substantially insoluble organic substrates (approximately 10%) and the highest proportion of soluble substrates (approximately 90%), showed the greatest weight loss and appeared to provide for most aggressive substrate-release profile over the two-month observation period. The "SRC-5" composition, which contained an intermediate blend of substantially insoluble and soluble substrates, exhibited an intermediate weight loss over the two-month observation period. These observations support the inventor's beliefs, and certain disclosures provided herein, that the solid-chemical compositions of the present invention provide improved means of achieving a variety of sustained-release profiles for organic substrates, which depending upon a variety of site-specific and contaminant-specific factors, provide end users of the present invention with a range of benefits and options for environmental remediation.

I claim:

1. A slow-release solid-chemical composition for environmental remediation which provides a sustained-release of organic substrates and complex inorganic phosphates, said sustained release being for a period of at least twenty-four hour, comprising:

a. a source of soluble organic substrates selected from the group consisting of sugars, soluble organic polymers and combinations thereof, in an amount of from about 7% to 90%, by weight percent, of said composition;

b. substantially insoluble organic substrates selected from the group consisting of fibrous plant materials, starches, cellulosic materials and combinations thereof, in an amount of from about 10% to 7%, by weight percent, of said composition;

c. complex inorganic phosphates selected from the group consisting of ringed metaphosphates, linear polyphosphates and combinations thereof, in an amount of from about 0.5% to 7%, by weight percent, of said composition; and d. soluble organic salts selected from the group consisting of lactates, formates, acetates, sorbates, citrates and combinations thereof, in an amount of from about 2% to 70%, by weight percent, of said composition.

2. The solid-chemical composition of claim 1, wherein said sugars are from a source selected from the group consisting of the powdered and granulated forms of white, brown and organic sugars, corn sugars, whole milk, low-fat milk, molasses, mannose, glucose, galactose, lactose, dextrose, xylose, arythrose, grain-malt extracts and combinations thereof.

3. The solid-chemical composition of claim 1, wherein said soluble organic salts are selected from the group consisting of calcium lactate, magnesium lactate, sodium formate, potassium formate, sodium acetate, calcium acetate, potassium acetate, sodium sorbate, potassium sorbate, sodium citrate, potassium citrate, citric acid salt and mixtures thereof.

4. The solid-chemical composition of claim 1, wherein said soluble organic polymers are selected from the group consisting of soluble corn starches, soluble tapioca starches, soluble grain starches, soluble potato starches, sodium carboxymethyl cellulose, hydroxypropyl cellulose, gum arabic, guar gum, carboxymethyl guar gum, hydroxypropyl guar gum, xanthan gum, carageenan, sodium alginate, potassium alginate, ammonium alginate, ammonium-calcium alginate, sodium-calcium alginate and combinations thereof.

5. The solid-chemical composition of claim 1, wherein said substantially insoluble organic substrates are selected from the group consisting of cellulose powder, microcrystalline cellulose, kenaf, sawdust, pectin, chitin, insoluble grain and vegetable starches, pre-gelled starches, insoluble grain and vegetable flours, fibrous plant materials, legume-derived plant materials, rice, cotton lint, recycled cotton fibers, shredded forms of recycled paper and cardboard and mixtures thereof.

6. The solid-chemical composition of claim 1, wherein said complex inorganic phosphates are selected from the group consisting of sodium hexametaphosphate, sodium trimetaphosphate, sodium tripolyphosphate, sodium-potassium tripolyphosphate, tetrasodium pyrophosphate and combinations thereof.

7. The solid-chemical composition of claim 1, further comprising an organic source of nutrient nitrogen.

8. The solid-chemical composition of claim 1, further comprising an organic source of nutrient nitrogen being plant materials selected from the group consisting of the plant families Leguminosae and Phaeophyta and combinations thereof, in an amount of from about 1% to 25%, by weight percent, of said composition.

9. The solid-chemical composition of claim 1, further comprising an organic source of nutrient nitrogen being plant materials selected from the group consisting of Lespedeza spp., Medicago spp., Vicia spp., Glycine spp., Lathyrus spp., Trifoliurn spp., Sargassum spp. and combinations thereof, in an amount of from about 1% to 25%, by weight percent, of said composition.

10. The solid-chemical composition of claim 1, further comprising an organic source of nutrient nitrogen consisting of alfalfa meal, in an amount of from about 1% to 25%, by weight percent, of said composition.

11. The solid-chemical composition of claim 1, further comprising an inorganic source of nutrient nitrogen, in an amount of from about 0.1% to 50%, by weight percent, of said composition.

12. The solid-chemical composition of claim 1, further comprising an ammonium-free source of inorganic nutrient nitrogen selected from the group consisting of sodium nitrate, sodium-potassium nitrate, potassium nitrate and combinations thereof.

13. The solid-chemical composition of claim 1, further comprising simple inorganic phosphates selected from the group consisting of sodium phosphate, calcium phosphate, dicalcium phosphate, potassium phosphate, and sodium-potassium phosphate and combinations thereof, in an amount of from about 0.1% to 10%, by weight percent, of said composition.

14. The solid-chemical composition of claim 1, further comprising a chelating agent selected from the group consisting of citric acid, sodium citrate, potassium citrate, humic acid, fulvic acid, nitrilotriacetic acid (NTA), ethylenediaminetetraacetic acid (EDTA) and combinations thereof, in an amount of from about 0.01% to 5%, by weight percent, of said composition.

15. The solid-chemical composition of claim 1, further comprising a pH buffering agent selected from the group consisting of calcium carbonate, lime, limestone, siderite and ferrous carbonate, rhodochrosite and manganese carbonate, calcium phosphate, sodium bicarbonate, portland cement, metal oxides, metal hydroxides, metal oxyhydroxides and combinations thereof, in an amount of from about 0.1% to 10%, by weight percent, of said composition.

16. The solid-chemical composition of claim 1, further comprising a disintegrant selected from the group consisting of pre-gelled starch, sodium starch glycolate, crosscarmelose of sodium, crospovidone and combinations thereof, in an amount of from about 0.01% to 5%, by weight percent, of said composition.

17. The solid-chemical composition of claim 1, further comprising a lubricant selected from the group consisting of waxes, magnesium stearate, calcium stearate and other stearates, stearic acid, sodium stearyl fumarate, hydrogenated vegetable oil, corn starch and combinations thereof.

18. The solid-chemical composition of claim 1, further comprising a microbial inoculum, said microbial inoculum being a source of microorganisms, in an amount of from about 0.0001% to 2%, by weight percent, of said composition.

19. The solid-chemical composition of claim 1, further comprising a microbial inoculum, said microbial inoculum being a source of microorganisms wherein said microorganisms are selected from the group consisting of anaerobic bacteria, facultative bacteria, mycoplasmas, anaerobic fungi, yeasts and combinations thereof, in an amount of from about 0.0001to 2%, by weight percent, of said composition.

20. The solid-chemical composition of claim 1, further comprising a microbial inoculum, said microbial inoculum being a source of microorganisms wherein said microorganisms are selected from the group consisting of Bacillus spp., Rhizobium spp., Bradyrhizobium spp., Fibrobacter spp., Clostridium spp. Pseudomonas spp., Geobacterspp., Arthrobacter spp., Nocardia spp., Aspergillus spp., Trichoderma spp., Candida spp., Yarrowia spp. and combinations thereof, in an amount of from about 0.0001% to 2%, by weight percent, of said composition.

21. The solid-chemical composition of claim 1, further comprising a source of enzymes selected from the group consisting of organic polymer degrading enzymes, plant-material degrading enzymes and combinations thereof, in an amount of from about 0.001% to 5%, by weight percent, of said composition.

22. The solid-chemical composition of claim 1, further comprising a source of enzymes wherein said enzymes are further selected from the group consisting of cellulases, hemicellulases, lignocellulases, amylases, glucanases, proteases, chitinases, lipase and combinations thereof, in an amount of from about 0.001% to 5%, by weight percent, of said composition.

23. The solid-chemical composition of claim 1, further comprising a microbial inoculum, said microbial inoculum being a source of microorganisms wherein said microorganisms are selected from the group consisting of microorganisms that produce organic polymer degrading enzymes, microorganisms that produce plant-material degrading enzymes and combinations thereof, in an amount of from about 0.0001% to 2%, by weight percent, of said composition.

24. The solid-chemical composition of claim 1, further comprising a microbial inoculum, said microbial inoculum being a source of microorganisms, wherein said microorganisms have the capacity to produce enzymes selected from the group consisting of cellulases, hemicellulases, lignocellulases, amylases, glucanases, proteases, chitinases, lipases and combinations thereof and said microorganisms are in an amount of from about 0.0001% to 2%, by weight percent, of said composition.

25. The solid-chemical composition of claims 1, 2, 3, 4, 5, 6, 7, 8, 9, 10, 11, 12, 13, 14, 15, 16, 17, 18, 19, 20, 21, 22, 23 or 24 in the form of briquettes, pellets, tablets, capsules and combinations thereof.

26. A slow-release solid-chemical composition for environmental remediation which provides for a sustained-release source of organic substrates and complex inorganic phosphates, said sustained release being for a period of at least twenty-four hours, comprising:
 a. powdered molasses, in an amount of from about 2.5% to 50%, by weight percent, of said composition;
 b. powdered or granulated forms of sugars selected from the group consisting of corn sugar, white sugar, brown sugar, organic sugar and combinations thereof, in an amount of from about 5% to 65%, by weight percent, of said composition;
 c. powdered or granulated forms of milk, low-fat milk and combinations thereof, in an amount of from about 1% to 25%, by weight percent, of said composition;
 d. sodium carboxymethyl cellulose, in an amount of from about 0.25% to 50%, by weight percent, of said composition;
 e. sodium formate, in an amount of from about 2.5% to 65%, by weight percent, of said composition;
 f. cellulose powder, in an amount of from about 1% to 25%, by weight percent, of said composition;
 g. powdered grain starch, in an amount of from about 0.25% to 15%, by weight percent, of said composition;
 h. alfalfa meal, in an amount of from about 0.5% to 25%, by weight percent, of said composition;
 i. complex inorganic phosphates selected from the group consisting of sodium hexametaphosphate, sodium trimetaphosphate and combinations thereof, in an amount of from about 0.5% to 20%, by weight percent, of said composition;
 j. magnesium stearate, in an amount of from about 0.1% to 2%, by weight percent, of said composition;
 k. enzymes selected from the group consisting of organic polymer degrading enzymes, plant-material degrading enzymes and combinations thereof, in an amount of from about 0.0001% to 0.5%, by weight percent, of said composition; and
 l. microorganisms selected from the group consisting of microorganisms that produce organic polymer degrading enzymes, microorganisms that produce plant-material degrading enzymes and combinations thereof, in an amount of from about 0.0001% to 0.5%, by weight percent, of said composition.

27. A slow-release solid-chemical composition for environmental remediation which provides for a sustained-release of organic substrates and complex inorganic phosphates, said sustained release being for a period of at least twenty-four hours, comprising:
 a. a source of soluble organic substrates selected from the group consisting of sugars, soluble organic polymers and combinations thereof, in an amount of from about 7% to 90%, by weight percent, of said composition;
 b. substantially insoluble organic substrates selected from the group consisting of fibrous plant materials, starches, cellulosic materials and combinations thereof, in an amount of from about 10% to 70%, by weight percent, of said composition;
 c. complex inorganic phosphates selected from the group consisting of ringed metaphosphates, linear polyphosphates and combinations thereof, in an amount of from about 0.5% to 7%, by weight percent, of said composition;
 d. soluble organic salts selected from the group consisting of lactates, formates, acetates, sorbates, citrates and combinations thereof, in an amount of from about 2% to 70%, by weight percent, of said composition;
 e. enzymes selected from the group consisting of organic polymer degrading enzymes, plant-material degrading enzymes and combinations thereof, in an amount of from about 0.001% to 5%, by weight percent, of said composition; and
 f. microorganisms selected from the group consisting of microorganisms that produce organic-polymer degrading enzymes, microorganisms that produce plant-material degrading enzymes and combinations thereof, in an amount of from about 0.0001% to 2%, by weight percent, of said composition.

28. The solid-chemical composition of claim 26, or 27 in the form of granules, briquettes, pellets, tablets, capsules and combinations thereof.

29. A method for the slow release of soluble organic substrates into an environment for environmental remediation, said slow release being for at least twenty-four hours, said method comprising applying to said environment a slow-release solid-chemical composition of claim 1, 2, 3, 4, 5, 6, 7, 8, 9, 10, 11, 12, 13, 14, 15, 16, 17, 18, 19, 20, 21, 22, 23, 24, 25, 26 or 28.

* * * * *

UNITED STATES PATENT AND TRADEMARK OFFICE
CERTIFICATE OF CORRECTION

PATENT NO. : 6,620,611 B2
APPLICATION NO. : 09/755473
DATED : September 16, 2003
INVENTOR(S) : Eric Christian Hince It is certified that error appears in the above-identified patent and that said Letters Patent is hereby corrected as shown below:

Column 21, Line 1 (Claim 1b), the text "10% to 7%" should be changed to --10% to 70%--.

Signed and Sealed this

Sixth Day of February, 2007

JON W. DUDAS
*Director of the United States Patent and Trademark Office*